United States Patent
Wiegand et al.

(10) Patent No.: US 7,531,173 B2
(45) Date of Patent: *May 12, 2009

(54) OPHTHALMIC COMPOSITION OF A VEGF ANTAGONIST

(75) Inventors: Stanley J. Wiegand, Croton-on-Hudson, NY (US); Jingtai Cao, Chappaqua, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/998,746

(22) Filed: Nov. 30, 2007

(65) Prior Publication Data

US 2008/0085276 A1 Apr. 10, 2008

Related U.S. Application Data

(62) Division of application No. 11/346,009, filed on Feb. 2, 2006, now Pat. No. 7,303,748.

(60) Provisional application No. 60/649,232, filed on Feb. 2, 2005.

(51) Int. Cl.
- A61K 38/18 (2006.01)
- C07K 14/71 (2006.01)
- C12N 15/62 (2006.01)

(52) U.S. Cl. ............... 424/134.1; 424/192.1; 514/2; 514/12; 530/350; 536/23.4

(58) Field of Classification Search ............... None
See application file for complete search history.

(56) References Cited

U.S. PATENT DOCUMENTS

| | | | |
|---|---|---|---|
| 5,851,999 A | 12/1998 | Ullrich et al. | |
| 6,011,003 A | 1/2000 | Charnock-Jones | |
| 6,270,993 B1 | 8/2001 | Shibuya | |
| 6,897,294 B2 | 5/2005 | Davis-Smyth et al. | |

FOREIGN PATENT DOCUMENTS

| | | |
|---|---|---|
| WO | WO 97/44453 | 11/1997 |
| WO | WO 98/13071 | 4/1998 |
| WO | WO 99/13909 | 3/1999 |
| WO | WO 00/75319 | 12/2000 |
| WO | WO 03/072029 | 9/2003 |
| WO | WO 2004/106378 | 12/2004 |

OTHER PUBLICATIONS

Phillips, A.J. (2001). The challenge of gene therapy and DNA delivery. J. Pharm. Pharmacol. 53:1169-1174.*
Palù et al. (1999). In pursuit of new developments for gene therapy. J. Biotechnol. 68:1-13.*
Holash, J., et al., (2002) PNAS, 99(17):11393-11398.
Heidaran, M.A., et al., (1990) J. Biol. Chem. 265(31):18741-18744.
Cunningham, S.A., et al., (1997) Biochem. Biophys. Res. Comm. 231:596-599.
Fuh, G., et al., (1998) J. Biol. Chem. 273(18):11197-11204.
Wiesmann, C., et al., (1997) Cell, 91:695-704.
Barleon, B., et al., (1997) J. Biol. Chem. 272(16):10382-10388.
Davis-Smyth, T., et al., (1998) J. Biol. Chem. 273(6):3216-3222.
Wulff, C., et al., (2002) Endocrinology 143(7):2797-2807.
Yatoh, S., et al., (1998) Transplantation 66(11):1519-1524.
Cao, J., et al., (2004) Investigative Ophthalmolgy and Visual Science, 45(Suppl. 1):U922.

* cited by examiner

*Primary Examiner*—Christine J Saoud
*Assistant Examiner*—Jon M Lockard
(74) *Attorney, Agent, or Firm*—Valeta Gregg

(57) ABSTRACT

Methods of reducing or treating angiogenesis and/or inflammation associated with eye injury in a subject in need thereof, comprising administering an agent capable of blocking or inhibiting vascular endothelial growth factor (VEGF) are provided. The methods are useful for inhibiting or ameliorating eye injury, particularly acute or subacute corneal injury and feature local administration (for example, subconjunctival injection or eye drops).

2 Claims, 7 Drawing Sheets

OPHTHALMIC COMPOSITION OF A VEGF ANTAGONIST

CROSS-REFERENCE TO RELATED APPLICATIONS

This application is a divisional of U.S. Pat. application Ser. No. 11/346,009, filed 2 Feb. 2006, now U.S. Pat. No. 7,303,748, which claims the benefit under 35 USC § 119(e) of U.S. Provisional 60/649,232 filed 2 Feb. 2005, which applications are herein incorporated by reference.

BACKGROUND

1. Field of the Invention

The field of the invention is related to local administration of VEGF antagonists to treat eye-related diseases, disorders and injuries.

2. Description of Related Art

It has previously been reported that topical application of an anti-VEGF neutralizing antibody suppresses acute allograft rejection in a rat corneal transplant model (Yatoh et al. (1998) Transplantation 66(11):1519-24).

BRIEF SUMMARY OF THE INVENTION

The invention is based in part on the finding that local administration of an agent capable of blocking, inhibiting, or reducing the activity of vascular endothelial growth factor (VEGF) is useful in treating of angiogenesis and inflammation associated with eye injuries or infection.

In a first aspect, the invention features a method of treating an eye injury, comprising locally administering an effective amount of an agent capable of blocking or inhibiting vascular endothelial growth factor (VEGF)-mediated activity to a subject in need thereof, such that the eye injury is ameliorated or improved. Preferably, the eye injury is a corneal injury or conjunctival injury and the method of treatment reduces angiogenesis and inflammation associated with the eye injury.

In specific embodiments, the agent capable of blocking, inhibiting, or ameliorating VEGF-mediated activity is a VEGF antagonist comprising a fusion polypeptide selected from the group consisting of acetylated Flt-1(1-3)-Fc, Flt-1 $(1-3_{R \to N})$-Fc, Flt-1$(1-3_{AB})$-Fc, Flt-1$(2-3_{AB})$-Fc, Flt-1(2-3)-Fc, Flt-1D2-VEGFR3D3-Fc$\Delta$C1(a), Flt-1D2-Flk-1D3-Fc$\Delta$C1(a), and VEGFR1R2-Fc$\Delta$C1(a). In a specific and preferred embodiment, the VEGF trap is VEGFR1R2-Fc$\Delta$C1(a) (also termed VEGF trap$_{R1R2}$) comprising the nucleotide sequence set forth in SEQ ID NO: 1 and the amino acid sequence set forth in SEQ ID NO: 2. The invention comprises the use of a VEGF trap that is at least 90%, 95%, 98%, or at least 99% homologous with the nucleotide sequence set forth in SEQ ID NO: 1 and/or the amino acid sequence set forth in SEQ ID NO:2.

The method of the invention is useful to treat acute and sub-acute corneal injury or conjunctival injury. Acute corneal injury may be treated within 24 hours of occurrence, and includes corneal injury or conjunctival injury caused by a penetrating object, a foreign body, or a chemical or burn injury. A sub-acute injury may be treated up to two weeks post-injury and may include the above listed injuries as well as infectious etiologies.

In various embodiments, the eye injury is caused by trauma, e.g., surgical injuries, chemical burn, corneal transplant, infectious or inflammatory diseases.

Length of treatment will vary according to the injury, but treatment duration may be short, e.g., up to one month, and may include a 3-6 month observation period, during which retreatment may be provided.

Administration may also include a second agent, such as an immunosuppressive agent, for example, one or more of a corticosteroid, dexamethasone, or cyclosporin A.

Local administration includes, for example, administration of the VEGF antagonist in eye drops applied to the eye, or subconjunctival injection to the eye.

In a second aspect, the invention features a method of healing an eye injury, comprising locally administering an effective amount of an agent capable of blocking or inhibiting vascular endothelial growth factor (VEGF)-mediated activity to a subject in need thereof, such that the eye injury heals.

In a third aspect, the invention features a method of reducing or ameliorating angiogenesis associated with an eye injury, comprising locally administering an effective amount of an agent capable of blocking or inhibiting vascular endothelial growth factor (VEGF)-mediated activity to a subject in need thereof, such that the angiogenesis associated with the eye injury is reduced or ameliorated.

In a fourth aspect, the invention features a method of reducing or ameliorating inflammation associated with an eye injury, comprising locally administering an effective amount of an agent capable of blocking or inhibiting vascular endothelial growth factor (VEGF)-mediated activity to a subject in need thereof, such that the inflammation associated with the eye injury is reduced or ameliorated.

In a fifth aspect, the invention features an ophthalmic composition comprising a VEGF antagonist, for example the VEGF trap VEGFR1R2-Fc$\Delta$C1(a), in a pharmaceutically acceptable carrier. Such pharmaceutical compositions may be liquid, gel, ointment, salve, slow release formulations or other formulations suitable for ophthalmic administration. In various embodiments, the pharmaceutical composition is for local administration comprising a VEGF trap, buffer, stabilizer, isotonizer, and a pharmaceutical carrier. In a preferred embodiment, the pharmaceutical composition is administered in the form of eye drops. In specific embodiments, the pharmaceutically acceptable carrier comprises as least one ophthalmically acceptable excipient, wherein the ophthalmically acceptable excipient can reduce a rate of removal of the VEGF antagonist from the eye by lacrimation. In various preferred embodiments, the pharmaceutical composition has an effective residence time in the eye of about 2 to about 24 hours.

In other embodiments, the pharmaceutical composition is for subconjunctival administration such as subconjunctival injection and subconjunctival implantation.

In a sixth aspect, the invention features a method of administering a VEGF antagonist for treatment of angiogenesis and/or inflammation associated with eye injury or infection, comprising local administration by eye drops comprising a VEGF trap, or subconjunctival administration by injection or implantation.

Other objects and advantages will become apparent from a review of the ensuing detailed description.

DETAILED DESCRIPTION

Figure 1:
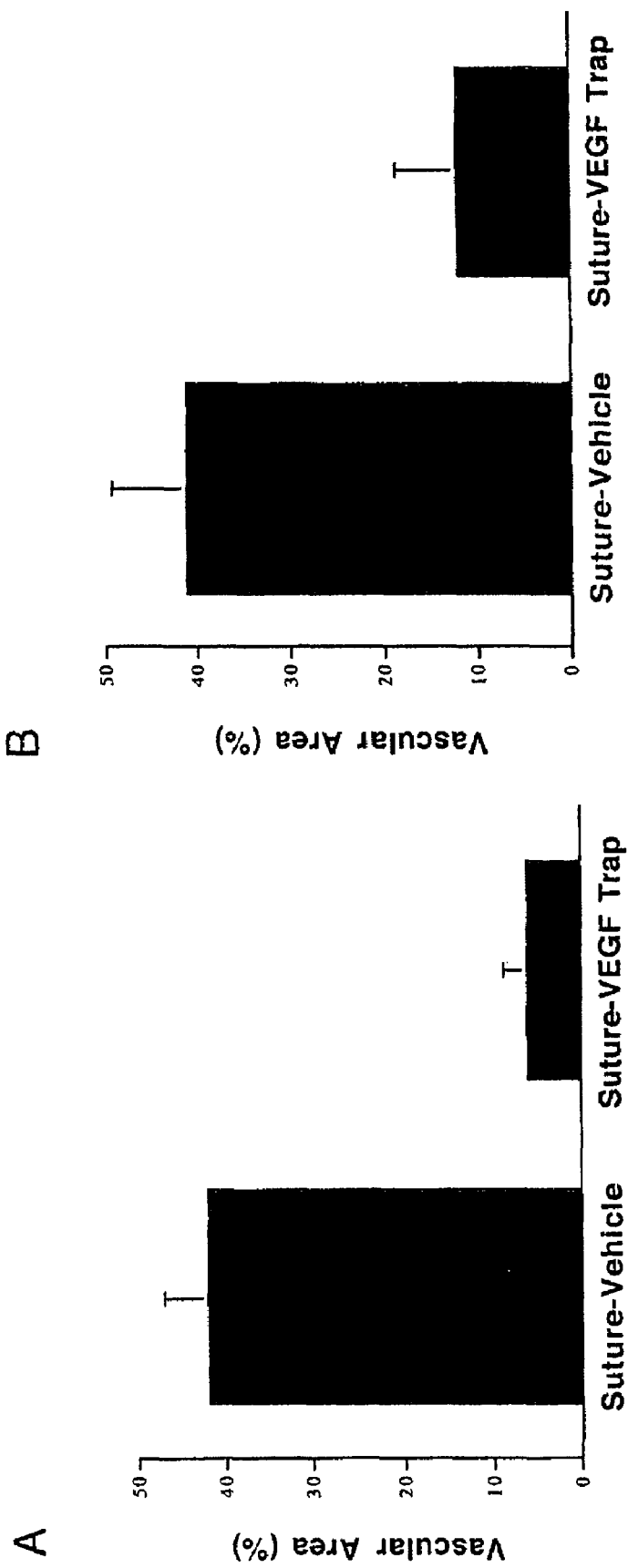
FIG. 1. Percent of vascularized corneal area in sutured mice subconjunctivally (SubC) treated with vehicle only or VEGF trap, at dosing regimens of (A) three 40 µg or (B) three 10 µg doses.

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein include the same meaning as commonly understood by one of ordinary skill in the art to which this invention belongs. Although any methods and materials similar or equivalent to those described herein can be used in the practice or testing of the present invention, preferred methods and materials are now described. All publications mentioned herein are incorporated herein by reference in their entirety.

General Description

Experiments were undertaken to evaluate corneal neovascularization after surgical suture placement in the cornea and to test whether corneal neovascularization following suture injury can be suppressed by local administration of an agent capable of blocking, inhibiting, or ameliorating VEGF-mediated activity. As described in the experimental section below, corneas of male C57BL/6 mice or Sprague-Dawley rats were suture-injured. A molecular trap designed to inhibit VEGF-A activity was administered locally and tested for its ability to suppress corneal vascularization. The results revealed that sutured cornea receiving subconjunctival administration of VEGF trap exhibited little or no neovascularization; corneal vascular area and vessel length following suture injury being comparable to that of a normal untreated (nonsutured) cornea. Treatment with VEGF trap eye drops following suture injury also effectively reduced neovascularization in suture-injured cornea.

In addition to quantification of neovascularization as measured by an increase in either blood vessel length or blood vessel area, suture-injury produced a marked influx of leucocytes into the injury site. When VEGF trap was administered locally either by subconjunctival injection (SubC) or by eye drop, a dramatic reduction in leucocyte infiltration was observed (data not shown).

In addition to the measurements reported below, serum levels of VEGF trap were determined in animals treated by subconjunctival injection or eye drops of VEGF trap. As evidenced by ELISA measurement for free VEGF trap in serum, there is little or no systemic exposure when VEGF trap is delivered at the effective doses by either of these local (SubC or eye drops) routes.

Definitions

The phrase "therapeutically effective dose" includes a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

The term "blocker", "inhibitor", or "antagonist" are used interchangeably to mean a substance that retards or prevents a chemical or physiological reaction or response. Common blockers or inhibitors comprise, but are not limited to, antisense molecules, antibodies, antagonists and their derivatives. More specifically, an example of a VEGF blocker or inhibitor includes a VEGF receptor-based antagonist comprising, for example, an anti-VEGF antibody, or a VEGF trap such as VEGFR1R2-FcΔC1(a) (SEQ ID NOs:1-2).

The phrase "ophthalmically acceptable" with respect to a formulation, composition or ingredient herein means having no persistent effect that is substantially detrimental to the treated eye or the functioning thereof, or on the general health of the subject being treated. It will be recognized that transient effects such as minor irritation or a "stinging" sensation are common with topical ophthalmic administration of drugs and the existence of such transient effects is not inconsistent with the formulation, composition or ingredient in question being "ophthalmically acceptable" as herein defined. However, preferred formulations, compositions and ingredients are those that cause no substantial detrimental effect, even of a transient nature.

VEGF Antagonists

In various embodiments, the VEGF trap is selected from the group consisting of acetylated Flt-1(1-3)-Fc, Flt-1(1-$3_{R \to N}$)-Fc, Flt-1(1-$3_{AB}$)-Fc, Flt-1(2-$3_{AB}$)-Fc, Flt-1(2-3)-Fc, Flt-1D2-VEGFR3D3-FcΔC1(a), Flt-1D2-Flk-1D3-FcΔC1(a), and VEGFR1R2-FcΔC1(a). For a more detailed description of these and other VEGF-receptor-based antagonists, including pegylated receptor-based blockers, see PCT WO/00/75319, the contents of which are incorporated in their entirety herein by reference.

In addition to the VEGF receptor-based antagonists disclosed in PCT WO/00/75319, which publication is herein specifically incorporated by reference in its entirety, variants and derivatives of such VEGF receptor-based blockers are also contemplated by the invention. The sequence of the variants or derivatives may differ by a change that can be one or more additions, insertions, deletions and/or substitutions of one or more nucleotides of the sequence set forth in SEQ ID NO:1. Changes to a nucleotide sequence may result in an amino acid change at the protein level, or not, as determined by the genetic code. Thus, nucleic acid according to the present invention may include a sequence different from the sequence shown in SEQ ID NO:1, yet encode a polypeptide with the same amino acid sequence as SEQ ID NO: 2. On the other hand, the encoded polypeptide may comprise an amino acid sequence which differs by one or more amino acid residues from the amino acid sequence shown in SEQ ID NO:2. A nucleic acid encoding a polypeptide which is an amino acid sequence variant or derivative of the sequence shown in SEQ ID NO:2 is further provided by the present invention. A nucleic acid encoding such a polypeptide may show at the nucleotide sequence and/or encoded amino acid level greater than about 90%, 95%, 98%, or 99% homology with the coding sequence shown in SEQ ID NO:1 and/or the amino acid sequence shown in SEQ ID NO:2. Amino acid "homology", may be understood to be similarity (according to the established principles of amino acid similarity, e.g. as determined using the algorithm GAP (Genetics Computer Group, Madison, Wis.)) or identity. GAP uses the Needleman and Wunsch algorithm to align two complete sequences that maximizes the number of matches and minimizes the number of gaps. Generally, the default parameters are used, with a gap creation penalty=12 and gap extension penalty=4.

Individual components of the VEGF-specific fusion proteins of the invention may be constructed by molecular biological methods known to the art with the guidance provided by the instant specification. These components are selected from a first cellular receptor protein, such as, for example, VEGFR1; a second cellular receptor protein, such as, for example, VEGFR2; and a multimerizing component, such as, for example, an Fc.

Specific embodiments of the VEGF-specific fusion proteins useful in the methods of the invention comprise a multimerizing component which allows the fusion proteins to associate, e.g., as multimers, preferably dimers. Preferably, the multimerizing component comprises an immunoglobulin-derived domain. Suitable multimerizing components are sequences encoding an immunoglobulin heavy chain hinge region (Takahashi et al. 1982 Cell 29:671-679); immunoglobulin gene sequences, and portions thereof.

The nucleic acid constructs encoding the fusion proteins useful in the methods of the invention can be inserted into an expression vector by methods known to the art, wherein the nucleic acid molecule can be operatively linked to an expression control sequence. Host-vector systems for the production of proteins comprising an expression vector introduced into a host cell suitable for expression of the protein are known in the art. The suitable host cell may be a bacterial cell such as *E. coli*, a yeast cell, such as, for example, *Pichia pastoris,* an insect cell, such as, for example, *Spodoptera frugiperda,* or a mammalian cell, such as, for example, a COS, CHO, 293, BHK or NS0 cell.

Methods of Administration

The invention comprises methods of treatment comprising administering to a subject an effective amount of an agent of the invention. In a preferred aspect, the agent is substantially purified (e.g., substantially free from substances that limit its effect or produce undesired side-effects). The subject is preferably an animal, e.g., such as cows, pigs, horses, chickens, cats, dogs, etc., and is preferably a mammal, and most preferably human.

Preferably, the pharmaceutical compositions of the invention are administered to the area in need of treatment by topical administration. Topical drug delivery is the most common treatment for diseases or disorders of the anterior segment of the eye, including, for example, corneal diseases, uveitis, and glaucoma. Topical delivery can be a safer and more convenient delivery method for patients, and can reduce the risk of many side effects observed in systemic treatment regimens. Topical administration of an angiogenesis inhibitor to the eye or cornea can be an effective treatment for treating neovascularization and/or inflammation. A preferred method of administering the pharmaceutical compositions of the invention to the eye is by eye drops comprising a VEGF trap.

In various preferred embodiments, the pharmaceutical compositions of the invention are administered to the area in need of treatment by subconjunctival administration. One preferred method of subconjunctival administration to the eye is by injectable formulations comprising a VEGF trap. Another preferred method of subconjunctival administration is by implantations comprising slow releasing VEGF trap.

Pharmaceutical Compositions

Pharmaceutical compositions useful in the practice of the method of the invention include a therapeutically effective amount of an active agent with a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Examples of suitable pharmaceutical carriers are described in "Remington's Pharmaceutical Sciences" by E. W. Martin. In a preferred embodiment, the composition is formulated in accordance with routine procedures as a pharmaceutical composition adapted for topical administration to human beings. Such pharmaceutical compositions may be liquid, gel, ointment, salve, slow release formulations or other formulations suitable for ophthalmic administration. The composition comprises an effective amount of VEGF antagonist and, optionally, at least one ophthalmically acceptable excipient, wherein the excipient is able to reduce a rate of removal of the composition from the eye by lacrimation, such that the composition has an effective residence time in the eye of about 2 hours to about 24 hours.

In various embodiments, compositions of the invention can comprise a liquid comprising an active agent in solution, in suspension, or both. The term "suspension" herein includes a liquid composition wherein a first portion of the active agent is present in solution and a second portion of the active agent is present in particulate form, in suspension in a liquid matrix. As used herein, liquid compositions include gels.

Preferably the liquid composition is aqueous. Alternatively, the composition can take form of an ointment. In a preferred embodiment, the composition is an in situ gellable aqueous composition, more preferably an in situ gellable aqueous solution. Such a composition can comprise a gelling agent in a concentration effective to promote gelling upon contact with the eye or lacrimal fluid in the exterior of the eye. Suitable gelling agents non-restrictively include thermosetting polymers such as tetra-substituted ethylene diamine block copolymers of ethylene oxide and propylene oxide (e.g., poloxamine 1307); polycarbophil; and polysaccharides such as gellan, carrageenan (e.g., kappa-carrageenan and iota-carrageenan), chitosan and alginate gums. The phrase "in situ gellable" includes not only liquids of low viscosity that can form gels upon contact with the eye or with lacrimal fluid in the exterior of the eye, but also more viscous liquids such as semi-fluid and thixotropic gels that exhibit substantially increased viscosity or gel stiffness upon administration to the eye or area surrounding the eye.

Aqueous compositions of the invention have ophthalmically compatible pH and osmolality. Preferably these compositions incorporate means to inhibit microbial growth, for example through preparation and packaging under sterile conditions and/or through inclusion of an antimicrobially effective amount of an ophthalmically acceptable preservative. Suitable preservatives non-restrictively include mercury-containing substances such as phenylmercuric salts (e.g., phenylmercuric acetate, borate and nitrate) and thimerosal; stabilized chlorine dioxide; quaternary ammonium compounds such as benzalkonium chloride, cetyltrimethylammonium bromide and cetylpyridinium chloride; imidazolidinyl urea; parabens such as methylparaben, ethylparaben, propylparaben and butylparaben, and salts thereof; phenoxyethanol; chlorophenoxyethanol; phenoxypropanol; chlorobutanol; chlorocresol; phenylethyl alcohol; disodium EDTA; and sorbic acid and salts thereof.

The composition can comprise an ophthalmic depot formulation comprising an active agent for subconjunctival administration. The ophthalmic depot formulation comprises microparticles of essentially pure active agent, e.g., the VEGF trap of SEQ ID NO:2. The microparticles comprising VEGF trap can be embedded in a biocompatible pharmaceutically acceptable polymer or a lipid encapsulating agent. The depot formulations may be adapted to release all of substantially all the active material over an extended period of time. The polymer or lipid matrix, if present, may be adapted to degrade sufficiently to be transported from the site of administration after release of all or substantially all the active agent. The depot formulation can be liquid formulation, comprising a pharmaceutical acceptable polymer and a dissolved or dispersed active agent, Upon injection, the polymer forms a deot at the injections site, e.g. by gelifying or precipitating.

The composition can comprise a solid article that can be inserted in a suitable location in the eye, such as between the eye and eyelid or in the conjunctival sac, where the article releases the active agent. Release from such an article is preferably to the cornea, either via lacrimal fluid that bathes the surface of the cornea, or directly to the cornea itself, with which the solid article is generally in intimate contact. Solid articles suitable for implantation in the eye in such fashion generally comprise polymers and can be bioerodible or non-bioerodible. Bioerodible polymers that can be used in preparation of ocular implants carrying a VEGF trap in accordance with the present invention include without restriction aliphatic polyesters such as polymers and copolymers of poly (glycolide), poly(lactide), poly(ε-caprolactone), poly(hydroxybutyrate) and poly(hydroxyvalerate), polyamino acids, polyorthoesters, polyanhydrides, aliphatic polycarbonates and polyether lactones. Illustrative of suitable non-bioerodible polymers are silicone elastomers.

The active agents of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

Combination Therapies

In various embodiments, the VEGF antagonists of the present invention may be administered in combination with one or more additional compounds or therapies or medical procedures. For example, suitable therapeutic agents for use in combination, either alternating or simultaneously, with the VEGF-binding fusion proteins of the invention, including topically administered immunosuppressive agents such as corticosteroids, dexamethasone, cyclosporin A, FK506, or anti-metabolic agents, (see Barker, N H, et al., (2000) Clin Exp Opthal 28:357-360). Other suitable therapeutic agents for use in combination, either alternating or simultaneously, with the VEGF antagonists of the invention may include agents that can block the biological activity of other VEGF family members such as VEGF-C and VEGF-D.

Kits

The invention also provides an article of manufacture comprising packaging material and a pharmaceutical agent contained within the packaging material, wherein the pharmaceutical agent comprises at least one VEGF-specific fusion protein of the invention and wherein the packaging material comprises a label or package insert that indicates that the VEGF-specific fusion protein can be used for treating eye injury. The kit can comprise a composition comprising a VEGF trap and one or more other components such as, for example, components to be combined prior to use either by a health care professional or by the subject. In one embodiment, the VEGF trap is combined with one or more components that can comprise, for example, a solution included in the kit to reconstitute a VEGF trap in the form of an ophthalmical composition suitable for topical or subconjunctival administration to a human or animal. Kit components can comprise, for example, normal saline solutions and/or solutions comprising one or more suitable pharmaceutical carriers, stabilizers, additives, or buffers. Preferably the kit comprises instructions for treatment or administration regimens and/or instructions for preparing or reconstituting a VEGF trap for use. The instructions can be in writing on paper, on computer media of any suitable type, as audiovisual materials including, for example, CD or DVD, or any other suitable format.

Other features of the invention will become apparent in the course of the following descriptions of exemplary embodiments which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1

Effect of Eye Drop Administration of VEGF Trap on Corneal Neovascularization

Topical administration at the cornea of a VEGF trap can effectively inhibit or reduce corneal neovascularization and/or inflammation of an injured cornea. Corneal injuries, such as those sustained on repeat penetrating keratoplasty and corneal graft procedures, can lead to inflammation and/or neovascularization of the cornea, sometimes resulting in corneal graft rejection.

A study of corneal neovascularization following suture injury in the presence and absence of topically administered VEGF trap was conducted. VEGF trap (SEQ ID NO:2) was administered in a pharmaceutical formulation for topical administration to the eye (i.e., VEGF trap eye drops) at pH 6.0 which contained 39.4 mg/ml VEGF trap in 5 mM phosphate, 5 mM citric acid, 100 mM NaCl, and 0.0005% Polysorbate 20. Male C57BL6 mice, 8-10 weeks old were used for the experiment. Each mouse underwent suture placement (three 10-0 nylon) in the peri-center of the right cornea under surgical microscope. The left cornea of each mouse was used as control. The mice were then placed in two groups: Each mouse in Group I received one normal saline eyedrop (4 microliters) (μl) on the right sutured cornea three times a day for eight days. Each mouse in Group II received one VEGF trap eye drop (4 μl) on the right sutured cornea three times a day for eight days. The saline eye drops contained 0.9% sodium chloride, Injection, USP, pH 5.6 (4.5-7.0) (Lot #01-172-JT, Abbott Laboratories, North Chicago, Ill.), where each 100 mL of the saline eye drops contained 900 mg NaCl in water. The VEGF trap eye drops contained 157.6 μg of VEGF trap/drop (4 μl/drop). On the eighth day, fluorescinated lectin (*Lycopersicon esculentum*) was injected intravenously to label the vasculature. Corneal flat-mounts were then prepared and the area of neovascularization measured.

The results demonstrate that sutured corneas receiving VEGF trap eye drops exhibited little or no corneal neovascularization relative to the total vascular area of the unsutured, untreated controls. In contrast, sutured mice treated with only normal saline exhibited marked neovascularization, showing about a four-fold increase in corneal vascular area. This study demonstrates that topical administration of VEGF trap almost completely suppresses corneal neovascularization following corneal suture placement. Topical administration of VEGF trap also effectively reduced inflammation induced by corneal injury. Thus, topical administration of a VEGF trap is a highly effective method of reducing or eliminating neovascularization and inflammation due to corneal disease, disorder, or injury.

Example 2

Effect of Subconjunctival Administration of VEGF Trap on Corneal Neovascularization in Rats The efficacy of subconjunctival delivery of a VEGF trap on corneal injury in the mammal was evaluated by observing the effects of subconjunctival delivery of a VEGF trap in suture-injured rat corneas. Neovascularization following corneal suture placement was measured in the presence and in the absence of subconjunctival delivery of a VEGF trap. Male Sprague-Dawley rats (200-250 g) underwent intrastromal suture placement (three 10-0 nylon sutures/eye) in the peri-center of the cornea. VEGF trap (SEQ ID NO:2) was injected subconjunctivally at dose of 200 μg in 50 μl per eye per day at day 0, day 2, and day 5 following suture placement. As a control, 50 μl of vehicle, lacking VEGF trap, was injected per eye at day 0, day 2, and day 5 following suture placement. On day 8 and day 12, corneal neovascularization was evaluated in corneal flat mounts. Representative corneas taken on day 8 also were fixed and embedded in paraffin. Sections were stained with hematoxylin and eosin. Leukocyte infiltration and corneal thickness were measured as indices of inflammation and edema, respectively.

The results showed that corneal flat mounts on day 8 from rats treated with subconjunctival administration of vehicle only displayed significant neovascularization in the vicinity of the corneal injury (i.e., in the vicinity of the sutures). Neovascularization developed from the limbal vessels to the three sutures in the peri-central cornea. Corneal flat mounts on day 8 from rats treated with subconjunctival administration of VEGF displayed very little neovascularization reflecting almost total inhibition of neovascularization.

Even seven days following the final subconjunctival injection of VEGF trap (i.e., even at day 12), corneal flat mounts displayed virtually no neovascularization. 12 day corneal flat mounts were made of sutured rats treated with subconjunctival administration of vehicle only, or VEGF trap. The sutured corneas treated with VEGF trap exhibited significant inhibition of neovascular proliferation, whereas corneas treated with vehicle only were still at peak neovascularization.

Histological analysis of corneas on day 8 revealed that suture-injured rats that received vehicle only displayed multiple layers of neovascular formation in the cornea, extensive leukocyte (inflammatory) cell infiltration of the cornea, and significant corneal thickening. In contrast, day 8 corneas of rats treated with subconjunctival injection of VEGF trap displayed substantially less infiltration of inflammatory cells, little or no corneal neovascularization, an a reduction in corneal thickening as compared to untreated injured rat corneas.

Example 3

Effect of Subconjunctival Administration of VEGF Trap on Corneal Neovascularization in Mice The efficacy of subconjunctival injection of the VEGF trap on neovascularization induced by corneal suture injury was evaluated further in mice using three dosing regimens. Male C57BL6 mice (8-10 weeks old) underwent suture placement (three 10-0 nylon sutures/eye) in the peri-central cornea. VEGF trap (SEQ ID NO:2) was injected subconjunctivally using the following dosing regimens: 40 μg on day 0, day 2, and day 5 following suture placement; 10 μg on day 0, day 2, and day 5 following suture placement; or 10 μg on day 0 following suture placement.

Using the above dosing regimens, mice were injected subconjunctivally with VEGF trap or vehicle only (no VEGF trap) and corneal flat mounts taken on day 9 were prepared and evaluated as described above.

The effect on day 9 of a subconjunctival VEGF trap dosing regimen of 40 micrograms on each of days 0, 2, and 5 following suture placement is shown in FIG. 1A. This dosing regimen effectively inhibits neovascularization, as measured by an increase in percent corneal vascular area (about 5% in uninjured, untreated mice, data not shown). The effect on day 9 of a subconjunctival VEGF trap dosing regimen of 10 μg on each of days 0, 2, and 5 following suture placement is shown in FIG. 1B which reveals that this dosing regimen also results in a decrease in corneal neovascular area compared with corneas treated with vehicle only (p<0.01).

Figure 2:
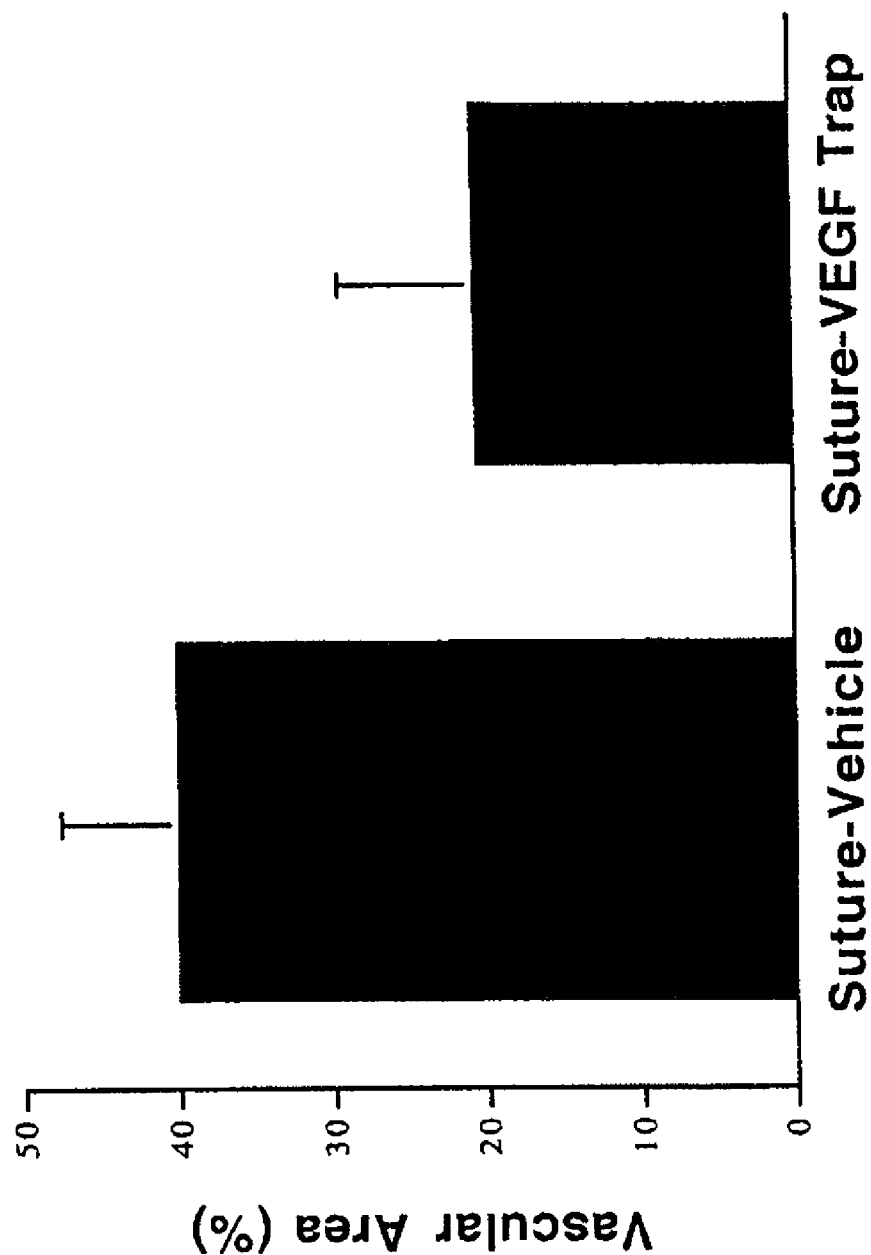
FIG. 2. Percent of neovascularized cornea at day 9 in sutured rats treated SubC with vehicle only or treated with VEGF trap, with a dosing regimen of 10 µg on the day of suturing.

The effect on day 9 of a single subconjunctival VEGF trap dose of 10 μg on the day of suture placement (FIG. 2) reveals that even a single subconjunctival dose of VEGF on the day of suturing can reduce neovascularization in the cornea by about half (p<0.05).

Example 4

Figure 3:
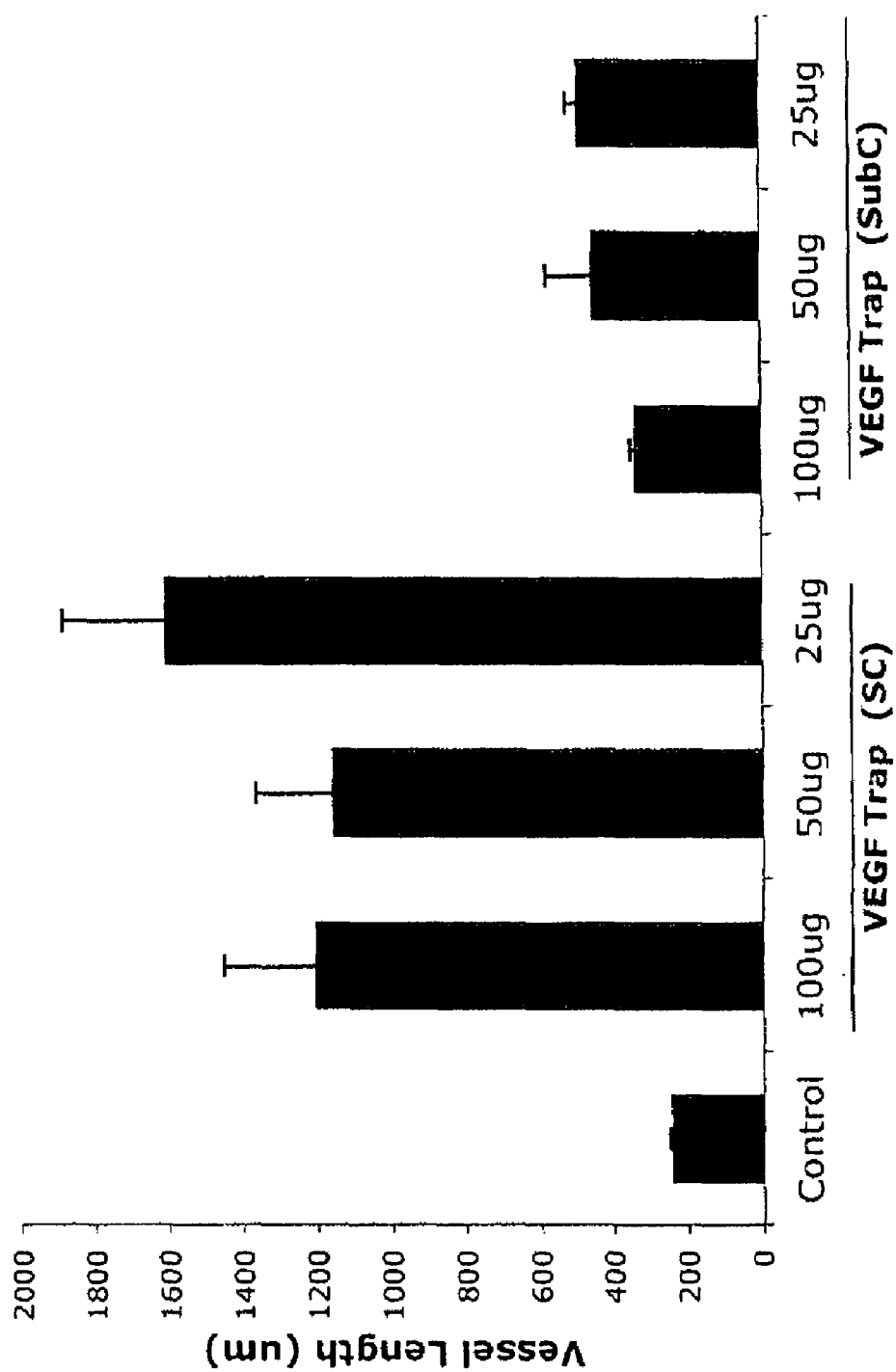
FIG. 3. Blood vessel length in sutured rats treated at day 0, 3 and 6 with 25, 50, or 100 µg VEGF trap injections administered subcutaneously (SC) or subconjunctivally (SubC). (Control=right non-sutured eye).

Effect of Systemic or Subconjunctival Administration of VEGF Trap on Corneal Neovascularization, Inflammation and Edema A study was conducted to determine the minimally effective dose of VEGF trap (SEQ ID NO:2) administered by systemic (subcutaneous, SC) injection, or local (subconjunctival, SubC) injection on corneal neovascularization, inflammation and edema. Male Sprague Dawley rats of approximately 250 g body weight received 3 loop sutures in the right cornea and the left eye was used as control. Six experimental groups (n=5 per group) received 3 SC or 3 SubC injections of VEGF trap (SEQ ID NO:2) at day 0, 3 and 6, at the following concentrations: 25 µg/50 µl, 50 µg/50 µl, or 100 µg/50 µl. The subconjunctival formulation was 4.92 mg/ml VEGF trap protein (SEQ ID NO:2) (Lot # VGTF00002T) in 5 mM phosphate, 5 mM citrate, 50 mM NaCl, 5% (w/v) sucrose, 0.1% polysorbate 20 (Tween=20), pH 6.0. Samples were harvested on day 9 for evaluation of corneal blood vessels in flat mounts stained with fluoresceinated concanavalin A. Evaluation included in-life slit-lamp examination and quantification of corneal neovascularization. Corneal neovascularization was quantified in concanavalin-stained flat mounts by measuring the increase in length of corneal blood vessels from the corneal limbus. The results, shown in FIG. 3, show that blood vessel length was significantly greater in the systemically injected (SC) animals relative to the locally injected (SubC) animals (p<0.001).

Example 5

Figure 4:
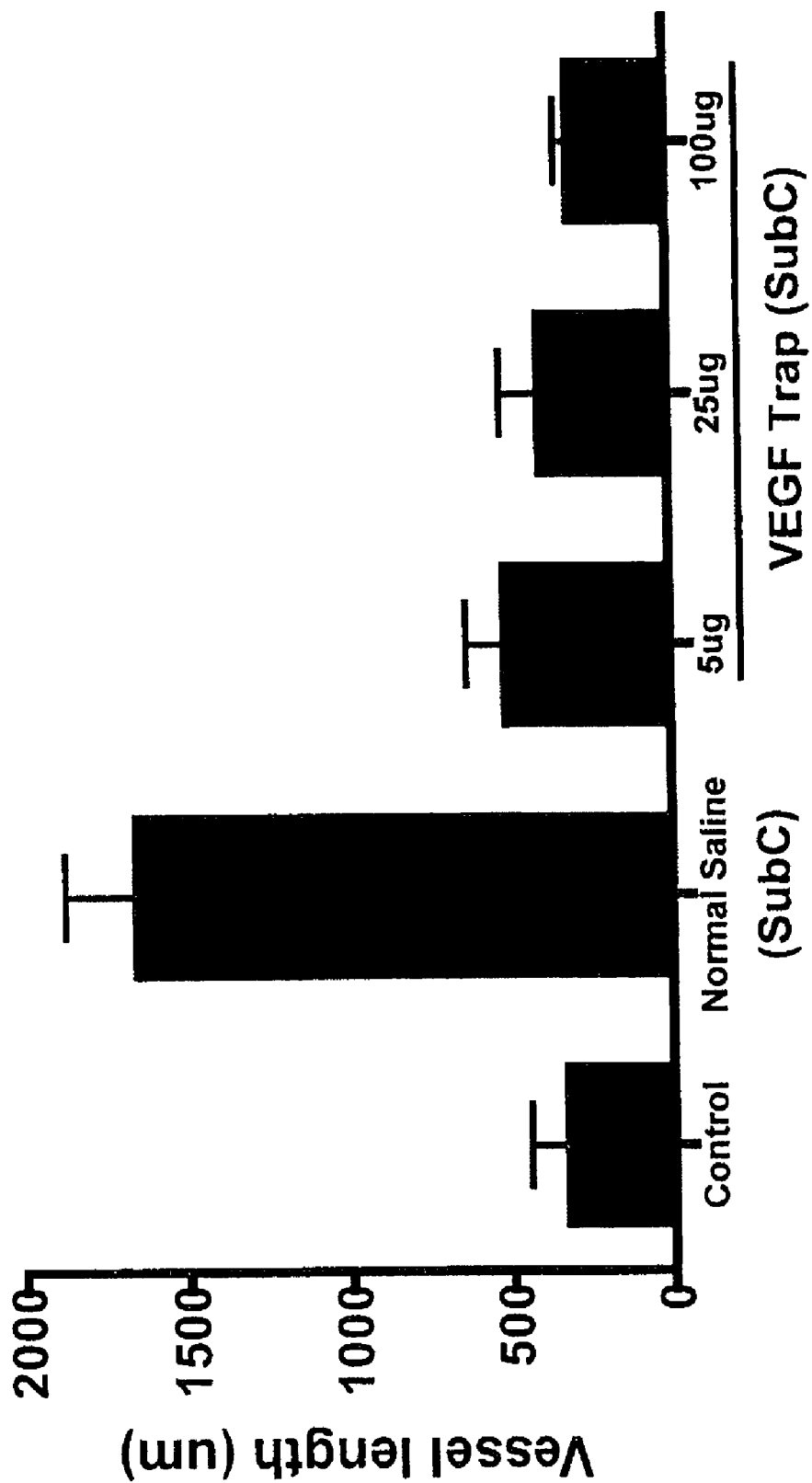
FIG. 4. Quantification of blood vessel length in sutured rats receiving subconjunctival normal saline, 5 µg, 25 µg, or 100 µg VEGF trap on day 0, 3 and 6. (Control=right non-sutured eye).

Effect of Subconjunctival Administration of VEGF Trap on Corneal Neovascularization, Inflammation and Edema A study was conducted as outlined above in male Sprague Dawley rats injected subconjunctivally on day 0, 3, and 6 with normal saline, 5 µg, 25 µg, or 100 µg of VEGF trap (SEQ ID NO:2). Eyes were harvested and examined as described above. FIG. 4 shows quantification of blood vessel length for each experimental group. Compared to the normal saline treated eyes, subconjunctival administration of VEGF trap significantly inhibited corneal neovascularization at all doses tested. The extent of inhibition was dose dependent (82%, 88% and 97% inhibition for 5 µg, 25 µg, and 100 µg, respectively).

Example 6

Figure 5:
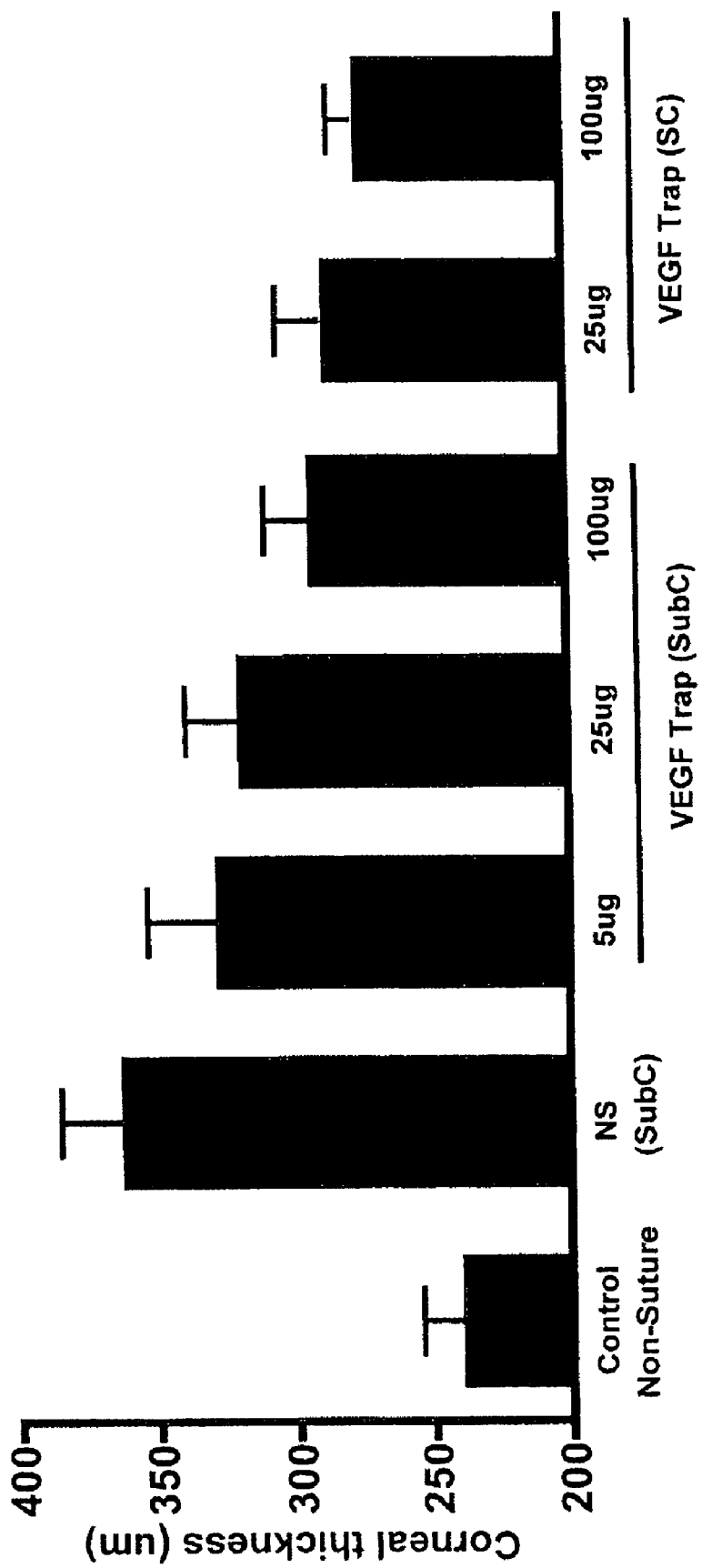
FIG. 5. Quantification of corneal edema as evidenced by corneal thickness in sutured rats receiving 25 or 100 µg VEGF trap SC or normal saline, 5 µg, 25 µg, or 100 µg VEGF trap SubC. (Control=right non-sutured eye) (NS=sutured eye, normal saline administered SubC).
Figure 6:
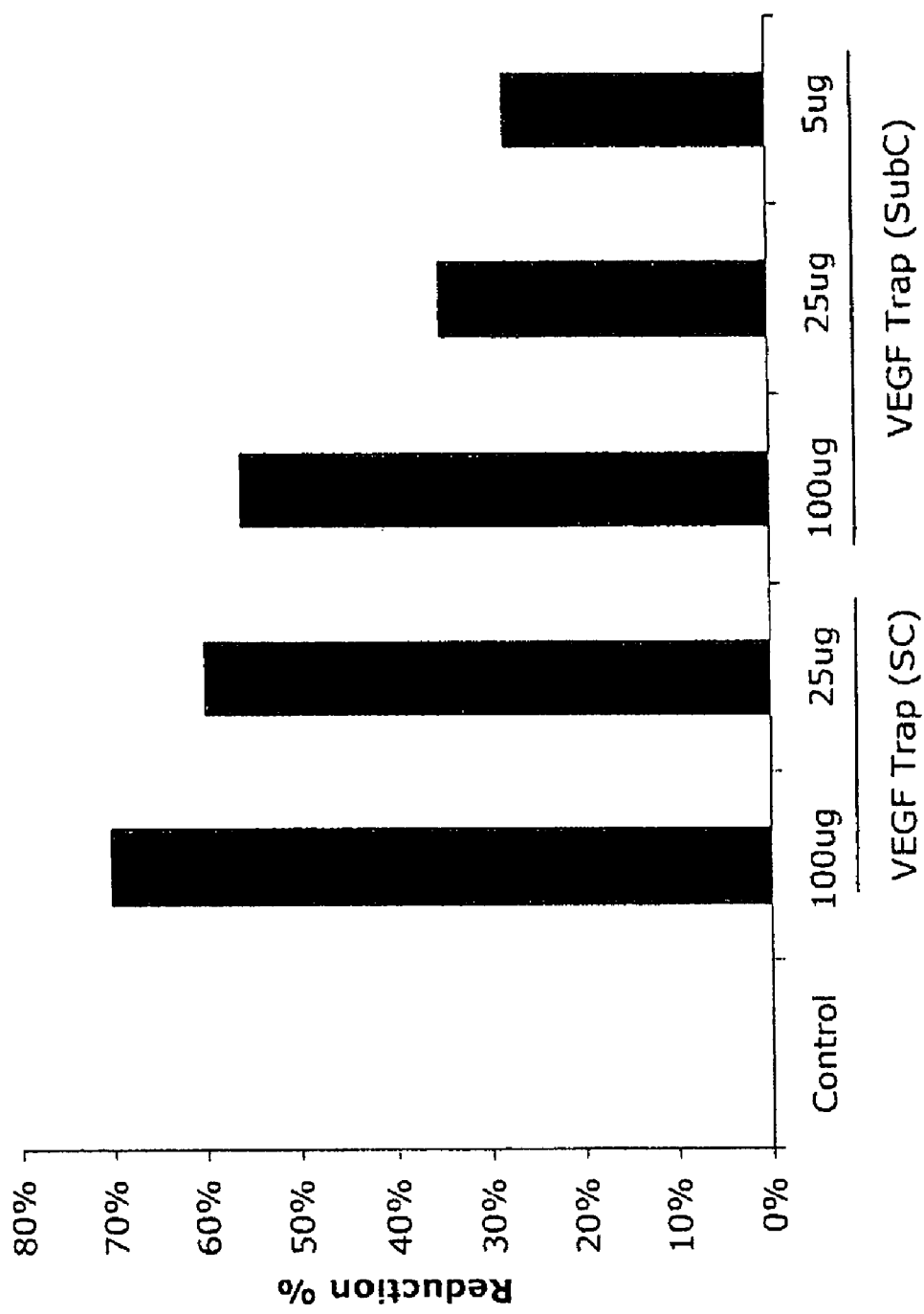
FIG. 6. Percent reduction of edema. Effect of VEGF trap on inflammation as determined by measurement of corneal thickness. All animals were sutured (control=sutured+systemic injection (SC) of normal saline).

Quantification of Corneal Edema in Animals Treated with Subconjunctival or Systemic Injections of VEGF Trap A study was conducted as described above. Male Sprague Dawley rats were injected subcutaneously with 25 or 100 µg VEGF trap or subconjunctivally with normal saline, 5 µg, 25 µg, or 100 µg VEGF trap. Injections were administered at day 0, 3 and 6. FIG. 5 shows quantification of corneal edema as evidenced by increased corneal thickness relative to the thickness of the cornea in normal, uninjured control. Compared to the saline treated group, subconjunctival administration of VEGF trap significantly reduced corneal thickness following suture injury in a dose dependent manner (28% to 56% reduction of excess corneal thickness). FIG. 6 shows the percent reduction of edema achieved with SC or SubC administration of the VEGF trap relative to control groups.

Example 7

Effect of Eye Drop Administration of VEGF Trap on Corneal Neovascularization Male C57BL6 mice, 8-10 weeks old, received suture placement (three 10-0 nylon sutures) in the peri-central right cornea. The topical eye drop formulation was 103.06 mg/ml VEGF trap protein (SEQ ID NO:2) (Lot #C04002M400) in 5 mM phosphate, 5 mM citric acid, 100 mM NaCl, 0.0005% polysorbate 20, pH 6.0. The animals were treated with eye drops topically applied to the sutured injured eye of each animal containing either vehicle or VEGF trap (412 µg/4 µl) three times per day for 9 days. Uninjured, untreated eyes served as controls. On day 9, animals received an intravenous injection of fluoresceinated lectin (*Lycopersicon esculentum*) and corneal flat-mounts were prepared for quantification of corneal neovascularization. Blood samples were taken and free VEGF trap levels measured by ELISA.

Figure 7:
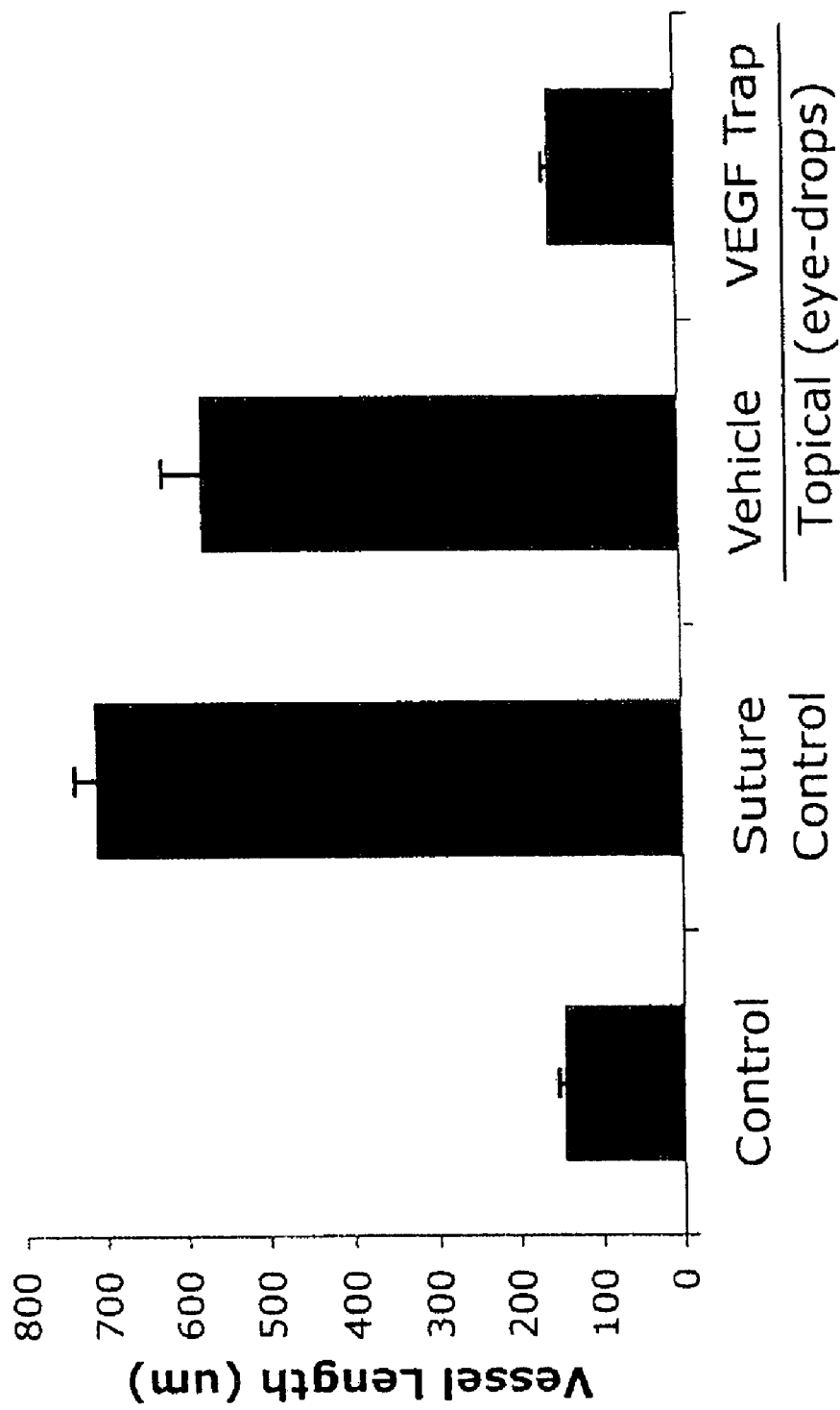
FIG. 7. Blood vessel length in suture-injury. Control=no suture injury. Suture control=suture+no treatment. Vehicle=suture-injury+vehicle provided as eye drops. VEGF trap=suture-injury+1 drop three times per day (412 µg VEGF trap protein/drop).

The effect of VEGF trap administered in eye drops is shown in FIG. 7. Topical administration of VEGF trap inhibited corneal neovascularization by 97% inhibition following suture placement at 9 days. Topical VEGF trap treatment also markedly reduced inflammation and edema induced by corneal injury.

The present invention may be embodied in other specific forms without departing from the spirit or essential attributes thereof.

We claim:

1. An ophthalmic composition comprising a vascular endothelial growth factor (VEGF) antagonist in a pharmaceutically acceptable carrier, wherein the VEGF antagonist is VEGFR1R2-FcΔC1(a) polypeptide.

2. The ophthalmic composition of claim 1, which is a liquid, gel, ointment, salve, or sustained release formulation.

* * * * *

SEQUENCE LISTING

```
<160> NUMBER OF SEQ ID NOS: 2

<210> SEQ ID NO 1
<211> LENGTH: 1377
<212> TYPE: DNA
<213> ORGANISM: homo sapiens

<400> SEQUENCE: 1
atggtcagct actgggacac cggggtcctg ctgtgcgcgc tgctcagctg tctgcttctc      60
acaggatcta gttccggaag tgataccggt agacctttcg tagagatgta cagtgaaatc     120
cccgaaatta tacacatgac tgaaggaagg gagctcgtca ttccctgccg ggttacgtca     180
cctaacatca ctgttacttt aaaaaagttt ccacttgaca ctttgatccc tgatggaaaa     240
```

```
cgcataatct gggacagtag aaagggcttc atcatatcaa atgcaacgta caaagaaata    300
gggcttctga cctgtgaagc aacagtcaat gggcatttgt ataagacaaa ctatctcaca    360
catcgacaaa ccaatacaat catagatgtg gttctgagtc cgtctcatgg aattgaacta    420
tctgttggag aaaagcttgt cttaaattgt acagcaagaa ctgaactaaa tgtggggatt    480
gacttcaact gggaataccc ttcttcgaag catcagcata agaaacttgt aaaccgagac    540
ctaaaaaccc agtctgggag tgagatgaag aaattttttga gcaccttaac tatagatggt    600
gtaacccgga gtgaccaagg attgtacacc tgtgcagcat ccagtgggct gatgaccaag    660
aagaacagca catttgtcag ggtccatgaa aaggacaaaa ctcacacatg cccaccgtgc    720
ccagcacctg aactcctggg gggaccgtca gtcttcctct ccccccaaa acccaaggac    780 accctcatga tctcccggac ccctgaggtc acatgcgtgg tggtggacgt gagccacgaa    840
gaccctgagg tcaagttcaa ctggtacgtg gacggcgtgg aggtgcataa tgccaagaca    900
aagccgcggg aggagcagta acagcacg taccgtgtgg tcagcgtcct caccgtcctg    960
caccaggact ggctgaatgg caaggagtac aagtgcaagg tctccaacaa agccctccca   1020
gcccccatcg agaaaaccat ctccaaagcc aaagggcagc cccgagaacc acaggtgtac   1080
accctgcccc catcccggga tgagctgacc aagaaccagg tcagcctgac ctgcctggtc   1140
aaaggcttct atcccagcga catcgccgtg gagtgggaga gcaatgggca gccggagaac   1200
aactacaaga ccacgcctcc cgtgctggac tccgacggct ccttcttcct ctacagcaag   1260
ctcaccgtgg acaagagcag gtggcagcag gggaacgtct tctcatgctc cgtgatgcat   1320
gaggctctgc acaaccacta cacgcagaag agcctctccc tgtctccggg taaatga      1377
```

<210> SEQ ID NO 2
<211> LENGTH: 458
<212> TYPE: PRT
<213> ORGANISM: homo sapiens

<400> SEQUENCE: 2

```
Met Val Ser Tyr Trp Asp Thr Gly Val Leu Leu Cys Ala Leu Leu Ser
 1               5                  10                  15

Cys Leu Leu Leu Thr Gly Ser Ser Ser Gly Ser Asp Thr Gly Arg Pro
            20                  25                  30

Phe Val Glu Met Tyr Ser Glu Ile Pro Glu Ile Ile His Met Thr Glu
        35                  40                  45

Gly Arg Glu Leu Val Ile Pro Cys Arg Val Thr Ser Pro Asn Ile Thr
    50                  55                  60

Val Thr Leu Lys Lys Phe Pro Leu Asp Thr Leu Ile Pro Asp Gly Lys
65                  70                  75                  80

Arg Ile Ile Trp Asp Ser Arg Lys Gly Phe Ile Ile Ser Asn Ala Thr
                85                  90                  95

Tyr Lys Glu Ile Gly Leu Leu Thr Cys Glu Ala Thr Val Asn Gly His
            100                 105                 110

Leu Tyr Lys Thr Asn Tyr Leu Thr His Arg Gln Thr Asn Thr Ile Ile
        115                 120                 125

Asp Val Val Leu Ser Pro Ser His Gly Ile Glu Leu Ser Val Gly Glu
    130                 135                 140

Lys Leu Val Leu Asn Cys Thr Ala Arg Thr Glu Leu Asn Val Gly Ile
145                 150                 155                 160

Asp Phe Asn Trp Glu Tyr Pro Ser Ser Lys His Gln His Lys Lys Leu
                165                 170                 175
```

-continued

```
Val Asn Arg Asp Leu Lys Thr Gln Ser Gly Ser Glu Met Lys Lys Phe
            180                 185                 190

Leu Ser Thr Leu Thr Ile Asp Gly Val Thr Arg Ser Asp Gln Gly Leu
        195                 200                 205

Tyr Thr Cys Ala Ala Ser Ser Gly Leu Met Thr Lys Lys Asn Ser Thr
    210                 215                 220

Phe Val Arg Val His Glu Lys Asp Lys Thr His Thr Cys Pro Pro Cys
225                 230                 235                 240

Pro Ala Pro Glu Leu Leu Gly Gly Pro Ser Val Phe Leu Phe Pro Pro
                245                 250                 255

Lys Pro Lys Asp Thr Leu Met Ile Ser Arg Thr Pro Glu Val Thr Cys
            260                 265                 270

Val Val Val Asp Val Ser His Glu Asp Pro Glu Val Lys Phe Asn Trp
        275                 280                 285

Tyr Val Asp Gly Val Glu Val His Asn Ala Lys Thr Lys Pro Arg Glu
    290                 295                 300

Glu Gln Tyr Asn Ser Thr Tyr Arg Val Val Ser Val Leu Thr Val Leu
305                 310                 315                 320

His Gln Asp Trp Leu Asn Gly Lys Glu Tyr Lys Cys Lys Val Ser Asn
                325                 330                 335

Lys Ala Leu Pro Ala Pro Ile Glu Lys Thr Ile Ser Lys Ala Lys Gly
            340                 345                 350

Gln Pro Arg Glu Pro Gln Val Tyr Thr Leu Pro Pro Ser Arg Asp Glu
        355                 360                 365

Leu Thr Lys Asn Gln Val Ser Leu Thr Cys Leu Val Lys Gly Phe Tyr
    370                 375                 380

Pro Ser Asp Ile Ala Val Glu Trp Glu Ser Asn Gly Gln Pro Glu Asn
385                 390                 395                 400

Asn Tyr Lys Thr Thr Pro Pro Val Leu Asp Ser Asp Gly Ser Phe Phe
                405                 410                 415

Leu Tyr Ser Lys Leu Thr Val Asp Lys Ser Arg Trp Gln Gln Gly Asn
            420                 425                 430

Val Phe Ser Cys Ser Val Met His Glu Ala Leu His Asn His Tyr Thr
        435                 440                 445

Gln Lys Ser Leu Ser Leu Ser Pro Gly Lys
    450                 455
```